United States Patent [19]

Gold et al.

[11] Patent Number: 5,275,812
[45] Date of Patent: Jan. 4, 1994

[54] METHOD OF TREATMENT FOR MYOCARDIAL INFARCTION

[75] Inventors: Herman K. Gold, Boston, Mass.; Barry S. Coller, Dix Hills, N.Y.; Desiré Collen, Winksele-Herent, Belgium

[73] Assignees: The General Hospital Corporation, Boston, Mass.; The Research Foundation of State University of New York, Stony Brook, N.Y.

[21] Appl. No.: 22,838

[22] Filed: Feb. 25, 1993

Related U.S. Application Data

[63] Continuation of Ser. No. 764,088, Sep. 23, 1991, abandoned, which is a continuation of Ser. No. 206,900, Jun. 14, 1988, abandoned, which is a continuation-in-part of Ser. No. 35,328, Apr. 7, 1987, abandoned, which is a continuation-in-part of Ser. No. 742,208, Jun. 7, 1985, abandoned, Ser. No. 742,187, Jun. 7, 1985, abandoned, and Ser. No. 851,711, Apr. 14, 1986, abandoned, which is a continuation-in-part of Ser. No. 745,415, Jun. 14, 1985, abandoned.

[51] Int. Cl.$^5$ ..................... A61K 39/395; C07K 15/28
[52] U.S. Cl. ............................... 424/85.8; 530/388.25
[58] Field of Search .................. 424/85.8; 530/388.25

[56] References Cited

U.S. PATENT DOCUMENTS

| | | | |
|---|---|---|---|
| 4,172,124 | 10/1979 | Kaprowski | 424/85.8 |
| 4,258,030 | 3/1981 | Sasaki et al. | 424/94.63 |
| 4,305,926 | 12/1981 | Everse et al. | 424/94.64 |
| 4,471,053 | 9/1984 | Comi et al. | 435/226 |
| 4,568,544 | 2/1986 | Hasegawa et al. | 424/85 |
| 4,772,585 | 9/1988 | Sarnoff et al. | 514/2 |

FOREIGN PATENT DOCUMENTS

| | | | |
|---|---|---|---|
| 0106812 | 4/1984 | European Pat. Off. | 424/94.63 |
| 0206532 | 12/1986 | European Pat. Off. | |
| 0206533 | 12/1986 | European Pat. Off. | |

OTHER PUBLICATIONS

Ganz, W., et al., J. Amer. Coll. Cardiol. 1:1247–1253, (1983).
Rentrop, K. P., et al., Amer. J. Cardiol. 54:29E–31E, (1984).
Gold, H. K., et al., Amer. J. Cardiol. 53:122C–125C, (1984).
Kunicki, T. J., et al., Blood Cells, 9:293–301 (1983).
Kunicki, T. J., et al., J. Immunol., 126:398–402 (1981).
Coller, B. S., et al., J. Lab. Clin. Med., 107: 384–392, 1986.
Coller, B. S., et al., Blood, 66: 1456–1459 (1985).
Kohler, H., et al., Nature, 256; 495–497, (1975).
Eldor, A., et al., Blood, 65:1477–1483 (1985).
Coller, B. S., et al., Blood, 68:783–786 (1986).
Garabedian, H. A., et al., J. Amer. Coll. Cardiol., 9:599–607 (1987).
Coller, B. S., et al., Blood, 61:99–110 (1983).
Oster, Z. H., et al., proc. Natl. Acad. Sci., (USA) 82:3465–3468 (1985).
Yesuda, T., et al., Clin. Res., 34:643A (1986).
Eisen, H. N., (In: Microbiology, 3rd ed., Davis, B. D., et al., Harper & Row, N.Y. pp. 342–349 (1980).
DiMinno, G., et al., Arteriosclerosis 6:203–211 (1986).
Coller, B. S., J. Clin. Invest., 76: 101–108, (1985).
Ganong, W. F., (In: Review of Medical Physiology, 9th ed., Lange, Los Altos, Calif., pp. 411–414 (1979).
Nachman, R. L., et al., J. Clin. Invest, 69: 263–269 (1982).
Coller, B. S., et al., J. Clin. Invest., 72: 325–338 (1983).
Gold, H. K., et al., Circulation, 68: Supp I, I-50–I-54 (1983).
Verstraete, M., et al., Lancet 1:142 (1985).
Gold, H. K., et al., Circulation, 73:347–352 (1986).
Callewaert, Chem Abs.; 103: 129039u, 1985.
Muzykantov et al., Chem Abs., 107: 81648c, 1986.
Ohlstein et al, Chem Abs, 107,: 32932z, 1987.

Primary Examiner—Robert A. Wax
Assistant Examiner—Susan A. Loring
Attorney, Agent, or Firm—Sterne, Kessler, Goldstein & Fox

[57] ABSTRACT

The present invention relates to a novel treatment for myocardial infarction which comprises administering a hapten-binding molecule capable of preventing reformation of fibrin-platelet clots and a thrombolytic agent capable of either dissolving fibrin-platelet clots or inhibiting their formation. The therapy of the invention is capable of increasing clot lysis while minimizing fibrinogen breakdown and preventing the reocclusion of the affected coronary artery. The therapy of the present invention is capable of achieving this goal even in the absence of heparin and when the concentration of thrombolytic agent is lower than that required by other potential therapies.

11 Claims, No Drawings

METHOD OF TREATMENT FOR MYOCARDIAL INFARCTION

This is a continuation of U.S. patent application Ser. No. 07/764,088, filed Sep. 23, 1991, now abandoned, which is a continuation of U.S. patent application Ser. No. 07/206,900filed Jun. 14, 1988, now abandoned, which is a continuation-in-part of U.S. patent application Ser. No. 035,328 (filed on Apr. 7, 1987) now abandoned, which is a continuation-in-part of U.S. patent applications Ser. Nos. 742,208 (filed on Jun. 7, 1985) now abandoned, 742,187 (filed on Jun. 7, 1985) now abandoned, and 851,711 now abandoned (filed on Apr. 14, 1986, which is a continuation-in-part of U.S. patent application Ser. No. 745,415, which application was filed on Jun. 14, 1985 now abandoned).

FIELD OF THE INVENTION

The present invention relates to a treatment for myocardial infarction, and more specifically to a therapy capable of preventing the reocclusion of a coronary artery which often accompanies the use of thrombolytic agents in the treatment of myocardial infarction. The therapy of the invention is capable of increasing clot lysis while minimizing fibrinogen breakdown and preventing the reocclusion of the affected coronary artery.

BACKGROUND OF THE INVENTION

The initiating event of many myocardial infarctions (heart attacks) is the hemorrhage into atherosclerotic plaque. Such hemorrhage often results in the formation of a thrombus (or blood clot) in the coronary artery which supplies the infarct zone (i.e., an area of coagulation necrosis which results from an obstruction of blood circulation). This thrombus is composed of a combination of fibrin and blood platelets. The formation of a fibrin-platelet clot has serious clinical ramifications. The degree and duration of the occlusion caused by the fibrin-platelet clot determines the mass of the infarct zone and the extent of damage.

A. Treatment for Myocardial Infraction

The primary goal of current treatment for myocardial infarction involves the rapid dissolution of the occluding thrombus and the restoration of blood flow ("reperfusion"). In order to be effective, a successful therapy must be capable of discriminating between a fibrin-platelet clot and the fibrin precursor, fibrinogen. The use of an agent which fails to exhibit such specificity may increase the risk of general hemorrhage to the patient. A successful therapy must further be capable of eliminating the fibrin-platelet clot in a manner which prevents its reformation after the cessation of therapy. If the fibrin-platelet clot is able to reform, then the affected artery may become reoccluded.

The formation of fibrin-platelet clots in other parts of the circulatory system may be partially prevented through the use of anti-coagulants (such as heparin). Unfortunately, heparin has not been found to be universally effective in preventing reocclusion in myocardial infarction victims in which the degree of blood vessel occlusion (the degree of "stenosis") is greater than or equal to 70%, particularly in those patients with severe residual coronary stenosis.

If an individual has formed a fibrin-platelet clot prior to the availability of medical assistance, the clot may be dissolved through the use of thrombolytic agents. A thrombolytic agent is a medicament capable of lysing the fibrin-platelet thrombus, and thereby permitting blood to again flow through the affected blood vessel. Such agents include streptokinase, prourokinase, urokinase, and tissue-type plasminogen activator (Ganz, W. et al., *J. Amer. Coll. Cardiol.* 1:1247-1253 (1983); Rentrop, K. P. et al., *Amer. J. Cardiol.* 54:29E-31E (1984); Gold, H. K. et al., *Amer. J. Cardiol.* 53:122C-125C (1984)).

Treatment with thrombolytic agents can often successfully restore coronary blood flow rapidly enough to interrupt myocardial infarction. Unfortunately, the dissolved fibrin-platelet clot has been found to reform after cessation of such thrombolytic therapy in a substantial number of patients. This reformation may result in the reocclusion of the affected blood vessels, and is, therefore, of substantial concern (Gold, H. K. et al., *Amer. J. Cardiol.* 53:122C-125C (1984); Gold, H. K. et al., *Circulation* 68:I-50-I-54 (1983)). Thus, although streptokinase treatment has been found to be successful in dissolving fibrin clots in approximately 85% of studied cases, reocclusion of the affected vessels has been found to occur in approximately 25% of the patients examined. (Gold, H. K., et al., *Circulation*, 68:I50-I54 (1983)).

Tissue-type plasminogen activator (t-PA) has been considered to be a more desirable thrombolytic agent than either streptokinase or urokinase because it displays greater (though not absolute) specificity for fibrin than does either of these agents (Verstrate, M., et al., *Lancet*, 1:142 (1985)). Tissue-type plasminogen activator (t-PA) is a clot-specific thrombolytic agent with a rapid disposition rate from plasma. Tissue-type plasminogen activator (t-PA) has been found to be an effective thrombolytic agent in patients with acute myocardial infarction, producing coronary reflow (i.e., decreasing stenosis) in 45-75 minutes in approximately 70% of patients studied (Gold, H. K. et al., *Circulation* 73:347-352 (1986)).

Tissue-type plasminogen activator is administered as an infusion at a rate of approximately 1-2 mg/kg patient weight/90 minutes. Because t-PA at high concentration is capable of breaking down fibrinogen, the use of higher dosages has been associated with an increased potential of general hemorrhage. Increased t-PA dosages have not been found to uniformly increase the rate of clot dissolution.

The benefit of employing t-PA is significantly offset by the spontaneous rate of acute reocclusion which follows the cessation of t-PA therapy. Gold, H. K. and coworkers have found that cessation of t-PA therapy resulted in reocclusion of affected blood vessels in approximately 45% of patients studied (*Circulation* 73:347-352 (1986)). Increased t-PA dosages have not been found to decrease the tendency for coronary artery reocclusion. Significantly, the possibility of thrombin clot reformation is closely related to the degree of residual coronary stenosis (i.e., the extent of blood vessel blockage). Thus, reocclusion is more probable in individuals in which high grade stenosis (i.e., greater than 70% quantitative stenosis or greater than 80% nonquantitative stenosis) has occurred. The reocclusion of blood vessels has been found to be inhibited by continued infusion of t-PA (Gold, H. K. et al., *Circulation* 73:347-352 (1986)). Unfortunately, the relatively short biological half-life of t-PA and the potential for increasing the tendency for severe bleeding in some patients may make continued infusion of t-PA impractical for many heart attack victims.

In summary, clinical investigations have shown that the dissolved thrombus frequently reforms following the cessation of t-PA infusion (Gold, H. K. et al., *Circulation* 73:347-352 (1986)), but that the frequency of such reocclusion can be minimized by providing a second ("maintenance") t-PA infusion of a substantially lower dose but for a substantially longer period. Heparin is currently recognized as the appropriate concommitant therapy for patients receiving such a maintenance infusion. The treatment of coronary artery thrombosis (clotting) with t-PA requires, therefore, a continuous infusion at a high rate in order to obtain rapid reperfusion, and a maintenance infusion at a lower dose to prevent reocclusion in patients with high grade residual stenosis.

B. Mechanism of Fibrin Clot Formation

Clots are composed of both fibrin and blood platelets in various ratios. The fundamental reaction in blood clotting involves the conversion of a soluble plasma protein (fibrinogen) into insoluble fibrin. The conversion of fibrinogen into fibrin is catalyzed by the enzyme, thrombin, which is a serine protease. The general mechanism of blood clot formation is reviewed by Ganong, W. F. (In: *Review of Medical Physiology*, 9th ed., Lange, Los Altos, Calif., pp. 411-414 (1979)). Platelets are disk-shaped structures present in blood. They contribute to clot formation by both their incorporation with fibrin into an insoluble mass and by their enhancement of the rate of fibrinogen to fibrin conversion. Platelets contribute to clot formation in myocardial infarction and are a major component of clots that reocclude coronary arteries that have been reperfused by treatment with a thrombolytic agent. The formation of the platelet aggregate depends upon an interaction between fibrinogen (and perhaps von Willebrand's factor or fibronectin) and a receptor molecule present on the surface of platelets. This platelet fibrinogen receptor has been found to be a complex of two membrane glycoproteins, termed GPIIb and GPIIIa (Nachman, R. L. et al., *J. Clin. Invest.* 69:263-269 (1982); Coller, B. S. et al., *J. Clin. Invest.* 72:325-338 (1983)). The specific role of the GPIIb/GPIIIa receptor complex was elucidated by Coller, B. S. and coworkers through their isolation of a murine monoclonal antibody (known as monoclonal antibody 10E5) found to be capable of binding to glycoproteins IIb and IIIa, and of completely blocking the binding of fibrinogen to platelets. In order to avoid potential complications due to the possibility that the monoclonal antibody's Fc fragment region might inhibit aggregation non-specifically, Coller, et al. used the F(ab')$_2$ fragment of the 10E5 antibody in their experiments. (Coller, B. S. et al., *J. Clin. Invest.* 72:325-338 (1983)). The F(ab')$_2$ fragment of an antibody includes only those regions of the antibody which are responsible for the antibody's specificity and antigen-binding capacity. The nature of F(ab')$_2$ fragments and procedures for their preparation are disclosed by Eisen, H. N. (In: *Microbiology*, 3rd ed., Davis, B. D. et al., Harper & Row, N.Y., pp. 342-349 (1980)).

DiMinno, G. et al. identified a monoclonal antibody (designated B79.7) which was specific for the platelet fibrinogen receptor, and which was capable of inhibiting aggregation and fibrinogen binding of platelets from individuals having familial hypercholesterolemia (FH) (DiMinno, G. et al., *Arteriosclerosis* 6:203-211 (1986)).

An additional monoclonal antibody (designated 7E3) was found to block the binding of fibrinogen to platelets, and to bind to GPIIb/GPIIIa (Coller, B. S., *J. Clin. Invest.*, 76:101-108 (1985)). This monoclonal antibody differed from antibody 10E5 in that it bound much more rapidly to activated platelets than to unactivated platelets and was capable of binding to canine as well as human platelets (Coller, B. S., *J. Clin. Invest.* 76:101-108 (1985); Coller, B. S. et al., *J. Lab. Clin. Med.*, 107:384-392 (1986); both of which references are incorporated by reference herein). The F(ab')$_2$ fragments of monoclonal antibody 7E3 were found to be capable of interfering with platelet aggregation, thus suggesting a potential therapeutic use in the treatment of thrombotic disease (Coller, B. S. et al., *Blood* 66:1456-1459 (1985)). The F(ab')$_2$ fragment of monoclonal antibody 7E3 was also found to be effective in blocking the accumulation of multiple layers of platelets without producing an unacceptable risk of hemorrhage, thus suggesting a potential use in avoiding the total occlusion of blood vessels which may occur in myocardial infarction and stroke (Coller, B. S. et al., *Blood* 66:1456-1459 (1985)).

C. Summary

In summary, a substantial goal of therapies aimed at treating myocardial infarction involves limiting necrosis by permitting early reperfusion and by preventing reocclusion. At present, this goal is partially achieved through the administration of thrombolytic agents capable of dissolving the potentially life-threatening fibrin-platelet clots. The potential benefit of employing such agents is, however, significantly offset by their lack of fibrin specificity (as in the case of streptokinase and urokinase), or by their relatively short biological half-life (which may result in reformation of the fibrin clot, and the accompanying reocclusion of the affected blood vessels). Hence, a need exists for an improvement in thrombolytic therapy which increases the rate of clot lysis, while minimizing fibrinogen breakdown and preventing reocclusion of the affected coronary artery.

SUMMARY OF THE INVENTION

The present invention provides an improved thrombolytic therapy for the treatment of myocardial infarction, and blood clots. In detail, the invention provides a method of treatment for myocardial infarction which comprises providing to a patient in need of such treatment:

(a) a hapten-binding molecule capable of preventing potential reformation of fibrin-platelet clots, in an amount sufficient to prevent such reformation; in combination with (b) a thrombolytic agent, in an amount sufficient to either (i) dissolve a fibrin-platelet clot or (ii) inhibit the formation of a fibrin-platelet clot; wherein the hapten-binding molecule (a) is different from the thrombolytic agent (b).

The invention additionally pertains to a kit useful for carrying out the above method being compartmentalized in close confinement to receive two or more container means therein, which comprises;

(1) a first container containing a therapeutically effective amount of the hapten-binding molecule (a); and (2) a second container containing a therapeutically effective amount of the thrombolytic agent (b).

DESCRIPTION OF THE PREFERRED EMBODIMENTS

The present invention involves a treatment for myocardial infarction which comprises providing a hapten-binding molecule and a thrombolytic agent to a recipient patient. A "hapten-binding molecule" is meant to refer to any molecule capable of binding to a hapten. Such molecules may include antibodies, antibody fragments (such as, for example, F(ab')$_2$ or F(ab) molecules), as well as any ligand capable of binding to a hapten.

The hapten-binding molecules of the present invention may be monoclonal antibodies or fragments thereof. It is especially preferable to employ the F(ab')$_2$ fragment of such an antibody for this purpose, in order to minimize any immunological reaction caused by the Fc portion of immunoglobulin and to prevent the development of thrombocytopenia by premature removal of antibody-coated platelets by splenic macrophages bearing receptors for the Fc portion of the molecule. Procedures for preparing monoclonal antibodies are disclosed by Kaprowski, H. et al. (U.S. Pat. No. 4,172,124); and Kohler et al. (*Nature* 256:495–497 (1975)). The formation of monoclonal antibodies capable of preventing the potential reformation of fibrin clots is disclosed by Coller, B. S. (*J. Clin. Invest.* 76:101–108 (1985)).

As used herein, a "hapten" is a molecule capable of being bound by an antibody. In order to be used in accordance with the present invention, the hapten-binding molecule must be capable of binding to a hapten present on the surface of platelets and thereby prevent such a platelet from aggregating with another platelet. Although any such hapten-binding molecule may be employed in accordance with the present invention, it is preferable to employ a hapten-binding molecule which is capable of binding to the platelet GPIIb or GPIIIa receptor proteins. It is most preferable to employ a hapten-binding molecule which is capable of binding to the platelet GPIIb/GPIIIa receptor complex. Examples of such hapten-binding molecules include antibodies 7E3, 10E5, and B79.7 (Coller, B. S. et al., *J. Clin. Invest.* 76:101–108 (1985); Coller, B. S. et al., *J. Clin. Invest.* 72:325–328 (1983); DiMinno, G. et al., *Arteriosclerosis* 6:203–211 (1986). Monoclonal antibody 7E3 is produced by a cell line deposited with the American Type Culture Collection, 12301 Parklawn Drive, Rockville, Md., 20852-1776 under the designation ATCC HB 8832.

The monoclonal antibodies which are useful in accordance with the present invention are preferably prepared according to the procedures set forth below:

Citrated platelet-rich plasma is prepared in accordance with the method of Coller et al. (*Blood* 47:841 (1976)), suspended in a suitable buffer and mixed with Freund's complete adjuvant. Injections of between about $1 \times 10^8$ to $5 \times 10^8$ washed platelets are injected intraperitoneally six times at weekly intervals into a BALB/c mouse and a seventh similar injection without adjuvant at a similar time interval is given intravenously. Three days later the mouse is killed, the spleen removed, the cells separated and fused with a BALB/c mouse myeloma line in accordance with the method of Levy et al. (*Curr. Top. Microbiol. Immunol.* 81:164 (1978)). In this method, the spleen cells and the myeloma cells in a ratio of 3.9:1 are pelleted together, the pellet is suspended in polyethylene glycol (35%) in RPMI 1640 medium whereupon the cells are immediately centrifuged at low velocity. The solution is then diluted to about 25% of its previous concentration with RPMI 1640, the cells resuspended, recentrifuged and the supernatant is removed. The supernatant is then incubated in a 5% $CO_2$ 95% air atmosphere in RPMI 1640 medium supplemented with fetal calf serum and thereafter selection is made in the usual manner by adding HAT medium and aliquoting into microtiter wells. After two weeks, the supernatant of the wells that show growth are screened for antifibrinogen receptor activity. The clone obtainable by this method are then selected for their ability to produce antibody capable of blocking or interfering with the aggregation of platelets.

The antibody is preferably isolated from the supernatant in the wells or flasks. Alternatively, the hybridomas can be injected intraperitoneally into Pristane$^R$ pretreated BALB/c rats and antibodies can be isolated from the ascitic fluid. The antibody may, preferably, be purified by precipitation with 50% saturated ammonium sulfate, followed by resuspension in between 5 and 10% of the original volume in sodium phosphate buffer and dialysis against the same buffer. Antibody may be further purified by chromatography using Protein A-Sepharose CL-4B equilibrated with phosphate buffer. Antibody may be eluted from such a column with phosphate buffer followed by decreasing pH 0.1M citrate buffers. Antibody 7E3, for example, elutes after the pH decreased to about 6.0. Protein elution may be monitored by ultraviolet spectroscopy at 280 nm.

Ouchterlony immuno-diffusion analysis against anti-IgG1, IgG2a, IgG2b, IgG3, IgM and IgA sera may be performed in order to determine the class of antibody obtained by the above-described procedures. Using such an analysis, it was determined that 7E3 antibody was of the IgG1 type.

Purified antibody, prepared in the manner described above, is preferably cleaved into active fragments in the following manner. Purified antibody is dialyzed overnight at reduced temperatures, suitably between 0 and 10° C. preferably at 4° C. against a slightly acidic saline buffer of pH 3.5–6.5, suitably about pH 4.0, after which freshly prepared pepsin is added in an amount equal to approximately 2% of the antibody's weight. The resulting solution is then incubated at about 37° C. for 12 to 24 hours. Digestion is stopped by dialyzing the solution against PBS, pH 7.4. The digestion is analyzed by polyacrylamide gel electrophoresis in order to determine whether the digestion is essentially complete.

Under somewhat different conditions, an Fab fragment can alternatively be prepared by digestion with papain (another proteolytic agent). In this method, antibody is incubated in the presence of 0.1M acetate, 2 mM EDTA, 1 mM cysteine and including 1% w/w of papain for 6–8 hours at 37° C. at a pH of 4.5–6, suitably 5.5.

The resulting F(ab')$_2$ fragment (such as, for example, the F(ab')$_2$ fragment of the 7E3 monoclonal antibody) can then be further purified by chromatography on a material such as Protein A Sepharose CL-4B or DE-52 in order to be certain that any remaining traces of the whole monoclonal antibody are removed.

The term "thrombolytic agent" is meant to refer to any agent capable of either dissolving a fibrin-platelet clot, or inhibiting the formation of such a clot. Examples of thrombolytic agents include streptokinase, prourokinase, urokinase, and tissue-type plasminogen activator. Although natural t-PA may be employed, it is preferable to employ recombinant t-PA. The invention may additionally employ hybrids, physiologically active fragments or mutant forms of the above thrombolytic agents. The term "tissue-type plasminogen activator" as used herein is intended to include such hybrids, fragments and mutants, as well as both naturally derived and recombinantly derived tissue-type plasminogen activator.

The hapten-binding molecule and the thrombolytic agent of the present invention are intended to be provided to the recipient in combination. Medicaments are considered to be provided "in combination" with one another if they are provided to the patient concurrently, or if the time between the administration of each medicament is such as to permit an overlap of biologic activity. It is preferable to provide the hapten-binding molecule to the patient prior to the administration of the thrombolytic agent. It is most preferable to provide the hapten-binding molecule between 5-20 minutes, and preferably between 8-12 minutes, prior to the administration of the thrombolytic agent.

The hapten-binding molecule of the present invention is provided with a goal of preventing potential reformation of fibrin-platelet clots. Such fibrin-platelet clots may, as discussed above, form as a consequence of the cessation of treatment with a thrombolytic agent. The reoccluding thrombi (clots) have been found to be rich in platelets, thus suggesting the possible efficacy of anti-platelet agents in preventing reocclusion. Such anti-platelet agents include aspirin, dipyridamole, as well as agents which interfere with the GPIIb/GPIIIa receptor of platelets. Platelet aggregation induced by agonists thought to operate in vivo, (e.g., ADP, epinephrine, thrombin, collagen, thromboxane A2) has been found to be absolutely dependent upon the binding of fibrinogen (and/or fibronectin and von Willebrand factor) to the GPIIb/IIIa receptor (Eldor, A. et al., *Blood* 65:1477-1483 (1985)). Thus, an agent capable of blocking both the binding of fibrinogen to the platelet and the platelet aggregate induced by an in vivo agonist could be used as the hapten-binding molecule of the present invention.

An amount of hapten-binding molecule capable of preventing partial reformation of a fibrin-platelet clot when provided to a patient is a "therapeutically effective" amount. In order to prevent potential clot reformation, it is desirable to provide between 0.01-2 milligram of hapten-binding molecule per kilogram of patient weight. This dosage may be administered, in one embodiment, over a period of between 75-105 minutes, by continual intravenous infusion. It is, however, most preferable to provide the hapten-binding molecule in an intravenously injectable bolus at a dose of between 0.01-0.8 mg/kg, and most preferably between 0.1-0.8 milligrams (of hapten-binding molecule) per kilogram of patient weight. If the hapten-binding molecule is provided in this manner, a single bolus is sufficient to prevent potential clot reformation. Although the hapten-binding molecule of the present invention may be dissolved in any physiologically tolerated liquid in order to prepare an injectable bolus, it is preferable to prepare such a bolus by dissolving the hapten-binding molecule in 0.15M NaCl.

The thrombolytic agent is provided in order to cause the lysis of an occluding thrombus. An amount of thrombolytic agent capable of causing such lysis is a "therapeutically effective" amount. The thrombolytic agent of the present invention is preferably provided at a dose of between 0.01-2.0 mg per kg of patient weight. In one embodiment, the thrombolytic agent is provided over a prolonged period (i.e., from about 60 to about 120 minutes). In a preferred embodiment, the thrombolytic agent of the present invention is provided as an intravenously injected bolus containing between 0.01-1.0 mg/kg, and most preferably between 0.1-1.0 mg/kg. The thrombolytic agent of the present invention may be dissolved in any physiologically tolerated liquid in order to prepare an injectable bolus. It is, however, preferable to prepare such a bolus by dissolving the thrombolytic agent in water.

A patient treated according to the preferred embodiment will, therefore, receive an intravenously injected bolus of the hapten-binding molecule in combination with an intravenously injected bolus of the thrombolytic agent. This preferred treatment minimizes the amount of t-PA required for thrombolysis, thus reducing the extent of fibrinogen breakdown and lessening any tendency for general hemorrhage. Importantly, the use of the preferred treatment results in the dissolution of the occluding thrombus at a rate which greatly exceeds the rate of thrombus dissolution when either the hapten-binding molecule or the thrombolytic agent is provided by infusion. Additionally, the risk of reocclusion is substantially reduced. A patient treated according to the preferred embodiment does not require heparin which is generally required with a maintenance infusion t-PA treatment.

These unexpected findings are important because it had previously not been possible to accelerate the rate of clot lysis without increasing the tendency to hemorrhage. The preferred embodiment, therefore, provides a method of treatment in which the administration of a bolus of a hapten-binding molecule in combination with the administration of a bolus of a thrombolytic agent are capable of dissolving an occluding thrombus at a faster rate than can be obtained when either compound is administered alone. Moreover, the preferred embodiment accomplishes this goal while minimizing both fibrinogen breakdown and the risk of reocclusion.

As would be apparent to one of ordinary skill in the art, the required dosage of the anti-hapten binding molecule or thrombolytic agent will depend upon the severity of the condition of the patient, and upon such criteria as the patient's height, weight, sex, age, and medical history.

The hapten-binding molecule or thrombolytic agent of the present invention can be formulated according to known methods to prepare pharmaceutically useful compositions, such as by admixture with a pharmaceutically acceptable carrier vehicle. Suitable vehicles and their formulation are described, for example, in Remington's Pharmaceutical Sciences (16th Ed., Osol, A. (ed.), Mack, Easton, Pa. (1980)). In order to form a pharmaceutically acceptable composition suitable for effective administration, such compositions will contain an effective amount of the hapten-binding molecule or thrombolytic agent, either alone, or with a suitable amount of carrier vehicle.

Additional pharmaceutical methods may be employed to control the duration of action. Control release preparations may be achieved by the use of polymers to complex or absorb the hapten-binding molecule or thrombolytic agents of the present invention. The controlled delivery may be exercised by selecting appropriate macromolecules (for example, polyesters, polyamino acids, polyvinyl pyrrolidone, ethylenevinylacetate, methylcellulose, carboxymethylcellulose, or protamine sulfate). The rate of drug release may also be controlled by altering the concentration of such macromolecules. Another possible method for controlling the duration of action comprises incorporating the therapeutic agents into particles of a polymeric substance such as polyesters, polyamino acids, hydrogels, poly(-lactic acid) or ethylene vinylacetate copolymers. Alternatively, it is possible to entrap the therapeutic agents in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system, for example, liposomes, albumin microspheres, microemulsions, nanoparticles, nanocapsules, or in macroemulsions. Such teachings are disclosed in Remington's Pharmaceutical Sciences (1980).

The thrombolytic agent or hapten-binding molecule may be provided to a patient by means well known in the art. Such means of introduction include oral means, intranasal means, subcutaneous means, intramuscular means, intravenous means, intra-arterial means, or parenteral means. In the most preferred method of treatment for myocardial infarction, a patient is provided with a bolus (intravenously injected) containing between 0.01-2.0 mg/kg.

Having now generally described this invention, the same will be better understood by reference to certain specific examples which are included herein for purposes of illustration only, and are not intended to be limiting of the invention, unless specified.

EXAMPLE 1

Preparation of Monoclonal Antibody 7E3

A BALB/c mouse (Jackson Laboratories, Bar Harbor, Me.) was injected intraperitoneally with six weekly 0.2 ml injections of $3 \times 10^8$ washed platelets (citrated PRP washed twice in 0.15M NaCl, 10 mM Tris/Cl, 10 mM EDTA, pH 74 [TS-E]), resuspended in 1/10 to 1/20 of their original volume in TS-E, and mixed 1:1 with complete Freund's adjuvant. The seventh weekly injection was given intravenously into the tail vein and consisted of 0.3 ml containing $5 \times 10^8$ washed platelets resuspended in T-S without EDTA. Each of the seven platelet suspensions was obtained from a different donor. Three days after the last injection, the mouse was killed by cervical dislocation and the spleen removed. A suspension of spleen cells in RPMI 1640 was prepared by teasing the spleen apart. After erythrocytes were lysed with ammonium chloride, the spleen cells were fused with a nonsecretory BALB/c mouse myeloma cell line (X63-Ag 8.653) that had been kept frozen in 10% DMSO, 90% fetal calf serum until one week before fusion, when it was thawed and maintained in the culture medium routinely used (RPMI 1640 supplemental with 10% fetal calf serum and 1,000 U of penicillin and 100 μg of streptomycin/ml). Fusion was carried out according to a modification of the method of Levy et al. (supra). Briefly, $2.7 \times 10^8$ spleen cells and $7 \times 10^7$ myeloma cells were pelleted together, the pellet was gently suspended in 2 ml of 35% polyethylene glycol in RPMI 1640 medium and the cells immediately centrifuged at 500 g at 22° C. for 6 minutes. The solution was then diluted with RPMI 1640 to 9% polyethylene glycol, the cells resuspended and immediately centrifuged at 230 g. for 6 minutes at 22° C. The supernatant fluid was then aspirated and the fused cells suspended in RPMI 1640 medium and supplemented with 20% fetal calf serum and 10% 109 medium (National Collection of Type Cultures). The cells were placed in a flask and incubated overnight at 37° C. in a 5% $CO_2$, 95% air atmosphere. The following day, the medium was made selective for successfully hybridized cells by adding hypoxanthine ($10^{-4}$M), aminopterin ($4 \times 10^{-7}$M), and thymidine ($1.6 \times 10^{-5}$M), after which the cells were aliquoted into 960 microtiter wells (Costar, Data Packaging, Cambridge, Mass.). Two weeks later, 574 wells showed growth and the supernatant fluids from 59 wells were positive in a screening assay for anti-fibrinogen receptor activity (see below). After an additional two weeks in culture, the positive clones were transferred to 24-well microtiter dishes (Costar) and fed with the same medium as above, but without the aminopterin. The clones were expanded and the cells that continued to produce anti-fibrinogen receptor antibody were suspended in 90% fetal calf serum-10% DMSO and frozen in liquid nitrogen.

The clones were subcloned by both limiting dilution technique and growth in soft agar to ensure monoclonality.

Ascitic fluid rich in 7E3 antibody was prepared by intraperitoneal injection of Pristane-pretreated BALB/c mice with $5 \times 10^6$ hybrid cells that had been washed twice in 0.15M NaCl, 10 mM sodium phosphate, pH 7.4 (PBS).

EXAMPLE 2

Screening Assay

35 μl of PRP (platelet rich plasma) (adjusted to $3 \times 10^{11}$ platelets/liter) and 35 μl of the supernatant culture medium (or ascitic fluid) to be assayed were incubated together for 2-60 minutes in a well of a round-bottomed microtiter plate (Linbro Chemical Co., Hamden, Conn.). 5 μl of the fibrinogen-coated bead suspension was then added and the plate was mixed on a rotator (Tekator V, American Scientific Products, Edison, N.J.) for 5 minutes at 280 rpm. The wells were observed from the bottom with the aid of a magnifying mirror apparatus (Cooke Microtiter System, Dynatech Laboratories, Inc., Alexandria, Va.). Wells containing culture medium that had not been used for growing cells showed marked agglutination of the beads (rated as 4+), whereas the supernatant culture medium or mouse ascitic fluid from positive clones inhibited the agglutination, resulting in lower readings (0-3+).

EXAMPLE 3

Antibody Purification

Culture supernatants were precipitated at 4° C. with 50% saturated ammonium sulfate and resuspended to between 1/20 and 1/10 of their original volume in 0.1M sodium phosphate buffer, pH 8.0. After dialysis against the same buffer, the samples were applied to a $0.8 \times 15.9$ cm column of Protein A Sepharose CL-4B that had been equilibrated with the phosphate buffer (after having been washed with both the phosphate buffer and a 0.1M citrate buffer, pH 3.0). The column was eluted with the phosphate buffer until the optical density of the eluate returned to base line, after which stepwise elution was accomplished with 0.1M citrate buffers of pH 6.0, 4.5, 3.5 and 3.0, as described by Ey et al. (*Immunochemistry* 15:429 (1978)). 7E3 immunoglobulins were eluted at pH 6.0. Protein elution was monitored by optical density at 280 nm and appropriate fractions were pooled and dialyzed against T-S containing 0.05% sodium azide. Antibody concentration was estimated by absorption at 280 nm, assuming $A^{1\%} = 15$.

EXAMPLE 4

Preparation of the F(ab')$_2$ Fragment of Monoclonal Antibody 7E3

Recombinant tissue-type plasminogen activator (rt-PA) was supplied by Genentech, Inc., South San Francisco, Calif. Two preparations were used: one (G11021) was predominantly two-chain rt-PA, and the other (G11035) was predominantly single-chain rt-PA. The production of monoclonal antibody 7E3, its purification, and fragmentation in F(ab')$_2$ fragments with pepsin are disclosed in Coller, B. S. et al. (*Blood* 66:1456–1459 (1986)); and Coller, B. S. et al. (*Blood* 68:783–786 (1986)), both of which references are incorporated by reference herein.

Antibody fragments were, preferably, prepared by a modified technique comprising fragmentation with 120 units of pepsin (Cooper Biomedical) per mg of antibody 7E3. The enzyme and antibody were incubated at a pH of 4.2 for 6 hours at 37° C. in 0.15 molar NaCl, 0.1M Na citrate. The digestion was stopped by raising the pH to 7.5 through the addition of 1M Tris HCl, 0.02M EDTA (pH 8.0). The F(ab')$_2$ fragments were purified by gel filtration using Superose 12 (Pharmacia, Piscataway, N.J.) which had been equilibrated with 0.15M NaCl, and by chromatography on Q-Sepharose Fast Flow (Pharmacia). Fractions were eluted by a linear gradient of 0 to 1.0M NaCl in 0.05M Tris HCl (pH 8.0). The final material was pooled and then both concentrated and diafiltered with 0.15M NaCl using a YM-10 filter (Amicon, Waltham, Mass.).

Antibody fragments were prepared at concentrations ranging from 0.68 to 3.1 mg/ml in 0.15M NaCl, and frozen until just before use. When analyzed for endotoxin with an amebocyte lysate clotting assay (Pyrogent, Mallinckrodt, St. Louis, Mo.), antibody prepared by the method of Coller, B. S. et al., were found to contain between 2 and greater than 80 endotoxins units/mg protein. Antibody prepared by the preferred method disclosed above had lower endotoxin values (0.5–1 endotoxin units/mg) as judged by a spectrophotometric assay (Whittaker, M. A. Bioproducts, Walkersville, Md.). A control F(ab')$_2$ fragment of a monoclonal antibody directed against an ovarian carcinoma antigen (OC-125) (Centocor, Malvern, Pa.) was prepared as described above with only minor modifications.

Antibody fragments were, alternatively, produced using the following method. Intact antibody, prepared as described above, were dialyzed overnight at approximately 4° C. against 0.2M sodium chloride, 0.2M acetate, pH 4.0, after which freshly prepared pepsin (1 mg/ml) was added in an amount equal to approximately 2% of the antibody's weight. The resulting solution was then incubated at about 37° C. for 12 to 24 hours. Digestion was stopped by dialyzing the solution against Phosphate Buffered Saline (PBS), pH 7.4. Analysis by polyacrylamide gel electrophoresis indicated that the digestion was essentially complete.

The resulting F(ab')$_2$ fragment of the 7E3 monoclonal antibody can then be purified by chromatography on a material such as Protein A Sepharose CL-4B or DE-52 in order to be certain that any remaining traces of the whole 7E3 monoclonal antibody are removed.

Platelet aggregation and $^{125}$I-7E3 binding studies were performed as described by Coller, B. S. et al. (*Blood* 66:1456–1459 (1986)). The number of F(ab')$_2$ molecules-bound per platelet, in vivo, was estimated from the ex vivo binding of $^{125}$I-7E3 to platelets, removed from dogs before and after the administration of the F(ab')$_2$ fragments.

EXAMPLE 5

An Animal Model for Coronary Artery Thrombosis

Mongrel dogs weighing approximately 20–25 kg were anesthetized with a slow intravenous injection of sodium pentobarbital, intubated and placed on an artificial ventilator. A left thoracotomy was performed in the 5th–6th intercostal space, and an arterial catheter was placed in the internal mammary artery for blood pressure monitoring. Procainamide (1.5 g injected intramuscularly in 2–3 sites) was then provided, the pericardium was opened, and a pericardial cradle was prepared. The left anterior descending coronary artery was dissected out from the epicardium, side branches were ligated, and a 2.5 cm segment was isolated. An electromagnetic flow probe (Carolina Medical Electronics FM501, King, N.C.) was placed on the most proximal portion of the segment and intravenous lidocaine (15 mg bolus followed by a constant infusion at 1 mg/min) was infused. A control left coronary angiogram was performed by injecting approximately 2 ml of Renograffin 76, by hand, through a modified Judkin's 7 French catheter inserted from a carotid artery. 1 ml of blood was then removed and kept in a syringe for later use in forming the thrombus, and heparin (5000 U intravenous bolus) was administered. Additional 1000 U boluses of heparin were administered at hourly intervals. A permanent 2 mm wide constrictor was placed near the distal end of the segment and adjusted so as to reduce coronary artery blood flow to approximately 40±10% of control.

High resolution post-mortem angiograms in selected animals showed that a constriction, so placed, decreased the luminal diameter by more than 90%. The 1 cm of coronary artery just proximal to the constriction was then emptied of blood and isolated between temporary silk snares. Intimal damage was induced by grasping the segment with forceps, and then the segment was flushed by releasing the proximal snare and injection of saline retrograde through a cannulated side branch. The segment was then reisolated and 0.2 ml of thrombin (Parke-Davis topical thrombin, 1000 U/ml, Morris Plains, N.J.) was introduced. 0.1 ml of the stored blood was injected into this isolated segment. After approximately 5 minutes, first the proximal and then the distal ties were released and the side branch catheter was removed. During this procedure, the permanent constrictor remained in place.

Approximately 30 minutes after injecting the thrombin and blood, and after a repeated angiogram confirmed the presence of a complete coronary artery occlusion, slow intravenous injections of the F(ab')$_2$ fragments (prepared as described in Example 4), acetylsalicylic acid (35 mg/kg) or dipyridamole (0.6 mg/kg) were administered. Approximately 10 minutes later, a 30-minute infusion of rt-PA (15 ug/kg/min for the two chain form G11021 or 30 ug/kg/min for the single chain form G11035) was initiated.

If partial coronary artery reperfusion had not occurred within the 30-minute infusion period, rt-PA infusion was continued for an additional 30 minutes. The blood flow in the affected vessel was monitored continuously. An angiogram was immediately performed after restoration of blood flow. The reperfusion time was taken as the number of minutes from the beginning of the rt-PA infusion until reperfusion was documented by the flow meter and confirmed by the repeat angiogram showing complete antegrade filling of the artery with rapid clearance of the dye (less than 4 cardiac cycles). After reperfusion was obtained, blood flow was monitored for evidence of reocclusion, with a final confirmation again obtained by angiography, using the same criteria as were used for establishing reperfusion. The reocclusion time was taken as the interval between documented reperfusion and reocclusion. The above described animal model closely simulates the response to thrombolytic therapy by human patients having acute myocardial infarction.

EXAMPLE 6

Analysis of Blood

Bleeding times were performed before and 30 min after injections of the F(ab')$_2$ fragment of 7E3 in 8 dogs with a spring-loaded blade device (Simplate, General Diagnostic, Morris Plains, N.J. or Surgicutt Int Technidyne Corp, Edison, N.J.), applied to a shaved foreleg. Venous blood samples for determination of the levels of fibrinogen, activated partial thromboplastin time, ADP-induced platelet aggregation and $^{125}$I-7E3 binding were collected into 0.01M citrate containing 150 KIU/ml aprotinin. (Sigma, St. Louis, Mo.) Platelet counts were performed on blood drawn into EDTA using an automated particle counter (Coulter, Hialeah, Fla.). Platelet-rich plasma was prepared for the aggregation and $^{125}$I-7E3 binding studies according to the method of Coller, B. S. et al. (*Blood* 66:1456-1459 (1986)). Plasma for the other studies was obtained from blood samples kept on ice until the end of the experiment, then centrifuged at 3000 g at 22 degrees C. for 10 min and stored at −20 degrees C.

EXAMPLE 7

Effect of Administration of Thrombolytic Agents

In order to assess the effectiveness of potential thrombolytic agents, the animal model disclosed in Example 5 was employed. Thus, a coronary artery was manipulated until blood flow was totally occluded. The subject animal then received either the F(ab')$_2$ fragment of monoclonal antibody 7E3, aspirin, or dipyridamole. After treatment with one of these agents, t-PA was administered and the time required for reperfusion was determined. After reperfusion had occurred, the animals were monitored to determine whether reocclusion of the affected blood vessel would occur.

Ten control animals were studied using the above described procedure, except that no 7E3 antibody fragment, aspirin or dipyridamole were provided. Of these ten animals, two were excluded from further analysis because one failed to achieve reperfusion despite 60 minutes of rt-PA infusion, and the second died immediately after reperfusion due to ventricular fibrillation. In the remaining 8 dogs, the permanent constriction reduced the blood flow to 38±10% of the control value before the acute thrombus was established and rt-PA was infused. The time to reperfusion was found to be 23±7 minutes (mean+SD). No significant differences were observed between the groups receiving the two different forms of rt-PA at the different infusion rates. Such a finding is consistent with the observation that the specific thrombolytic activity of the two-chain form is somewhat longer than that of the one-chain form (Garabedian, H. A. et al., *J. Amer. Coll. Cardiol.* 9:599-607 (1987)). After reperfusion, 7 of the 8 dogs rethrombosed rapidly with a mean time to reocclusion of 7±5 minutes. In some of these animals, cyclic reperfusion and reocclusion occurred during the infusion of rt-PA. Histologic examination of the affected vessels showed that the occlusion was due to platelet-rich thrombus. The results of this experiment are shown in Table 1.

TABLE 1

Efficacy of Thrombolytic Therapy Frequency of Reperfusion and Reocclusion in Animals Receiving Only rt-PA

| rt-PA | No. | Post-stenosis flow (% control) | Dose (ug/kg/min × min) | No. of dogs | Reperfusion time (min) | No. of dogs | Reocclusion time (min) |
|---|---|---|---|---|---|---|---|
| G11021 | 1 | 48 | 15 × 30 | | 33 | | 11 |
| | 2 | 43 | 15 × 30 | | 22 | | 5 |
| | 3 | 17 | 15 × 30 | | 34 | | 15 |
| G11035 | 4 | 33 | 30 × 30 | | 25 | | 8 |
| | 5 | 50 | 30 × 30 | | 26 | | >120 |
| | 6 | 40 | 30 × 30 | | 15 | | 4 |
| | 7 | 35 | 30 × 30 | | 17 | | 1 |
| | 8 | 40 | 30 × 30 | | 13 | | 2 |
| Total | 8 | 38 ± 10 | — | 8 | 23 ± 7 | 7 | 7 ± 5 |

Treatment with aspirin (acetyl salicylic acid) before infusion of two-chain rt-PA for 30-60 minutes caused reperfusion within 42±6 minutes in treated animals. Two of the four dogs thus treated suffered reocclusion rapidly (8 and 15 minutes, respectively), one reoccluded at 116 minutes, and one remained open for more than 120 minutes. Six dogs were treated with dipyridamole and two-chain rt-PA. The coronary arteries of five of these dogs reoccluded within 30 minutes, whereas the arteries of one dog remained open for greater than 55 minutes. The results of this experiment are shown in Table 2.

TABLE 2

Efficacy of Thrombolytic Therapy Frequency of Reperfusion and Reocclusion in Animals Treated with Acetyl Salicylic Acid (ASA) or Dipyridamole (DIP)

| Drug | No | Post-stenosis flow (% control) | Dose (ug/kg/min × min) | Reperfusion time (min) | Reocclusion time (min) |
|---|---|---|---|---|---|
| ASA | 1 | 40 | 15 × 30 | 44 | 116 |
| | 2 | 30 | 15 × 60 | 41 | >120 |
| | 3 | 33 | 15 × 60 | 32 | 15 |
| | 4 | 50 | 15 × 60 | 50 | 8 |
| DIP | 1 | 67 | 15 × 30 | 8 | 10 |
| | 2 | 62 | 15 × 30 | 11 | 10 |
| | 3 | 39 | 15 × 30 | 9 | >55 |
| | 4 | 48 | 15 × 30 | 10 | 11 |
| | 5 | 39 | 15 × 30 | 24 | 34 |
| | 6 | 55 | 15 × 30 | 9 | 7 |
| Total | | | | | |
| ASA | 4 | 38 ± 8 | — | 42 ± 7 | 65 ± 53 |
| DIP | 6 | 52 ± 11 | — | 12 ± 6 | 21 ± 18 |

EXAMPLE 8

Treatment With F(ab')₂ Fragments of Monoclonal Antibody 7E3 and rt-PA

Thirteen dogs received the F(ab')₂ fragments of antibody 7E3 at a dose of 0.7–0.8 mg/kg in combination with either 15 ug/kg/min (of two-chain rt-PA) or 30 ug/kg/min (of one-chain) rt-PA. Of these 13 animals, two achieved spontaneous reperfusion of the coronary arteries prior to the administration of rt-PA and a third dog failed to achieve reperfusion by angiographic criteria despite 60 minutes of rt-PA treatment. These three animals were eliminated from further analysis.

The left anterior descending coronary artery blood flow in the remaining 10 dogs was found to have decreased to an average of 37±11% of the control value by the permanent constrictor, a value not significantly different from that observed in the control group (38±10%). Reperfusion was found to occur after 14±10 minutes in this group, and none of the animals had coronary reocclusion during the observation period of approximately 2 hours. The results of the experiment are shown in Table 3.

Five of the six dogs treated with antibody prepared in the manner described by Coller, B. S. et al., *Blood* 66:1456–1459 (1986), sustained a transient decrease in blood pressure that responded to saline infusion. In contrast, none of the five animals treated with the antibody prepared as described in Example 4 became hypotensive, suggesting that the Coller et al. preparations were contaminated with a vasoactive agent, such as endotoxin.

As a control experiment, two dogs were injected with 0.8 mg/kg F(ab')₂ fragment of the monoclonal antibody OC-125 and infused with 30 ug/kg/min of single-chain rt-PA for 60 minutes. In one animal, reperfusion occurred after 36 minutes, and reocclusion within 29 minutes. In the second animal, reperfusion occurred after 60 minutes, and reocclusion occurred within 1 minute. This experiment shows that a combined treatment with rt-PA and the 7E3 F(ab')₂ fragment is effective in permitting reperfusion within 30 minutes, and in preventing reocclusion of blood vessels. Thus, this combination of medicaments provides an effective therapy for myocardial infarction. This therapy had two significant effects: first, it accelerated the rate at which reperfusion of effected blood vessels occurred after treatment with rt-PA. Second, it prevented the reocclusion of these blood vessels.

In summary, the 7E3 F(ab')₂ fragment, at a dose of 0.7–0.8 mg/kg was found to be efficacious in preventing reocclusion after successful reperfusion with rt-PA. Coronary arteries of 10 reperfused dogs remained open, whereas 7 of 8 control animals suffered reocclusion of their coronary arteries within 30 minutes after rt-PA treatment.

Significantly, the antibody was found to block only the receptor that mediates platelet aggregate formation, and to not affect other platelet receptors that probably mediate adhesion of platelets to the subendothelium. Thus, because the therapy may inhibit platelet aggregation without significantly inhibiting platelet adhesion and other platelet functions, the risk of hemorrhage may be decreased relative to other therapies that effect both platelet aggregation and adhesion.

TABLE 3

Efficacy of Thrombolytic Therapy Frequency of Reperfusion and Reocclusion in Animals Treated with the F(ab')₂ Fragment of Monoclonal Antibody 7E3

| rt-PA | No | Post-stenosis flow (% control) | Dose (ug/kg/min × min) | Reperfusion time (min) | Reocclusion time (min) |
|---|---|---|---|---|---|
| G11021 | 1 | 23 | 15 × 30 | 8 | >120 |
|  | 2 | 57 | 15 × 30 | 7 | >120 |
|  | 3 | 53 | 15 × 30 | 8 | >112 |
|  | 4 | 33 | 15 × 30 | 5 | >120 |
| G11035 | 1 | 36 | 30 × 30 | 8 | >120 |
|  | 2 | 45 | 30 × 30 | 36 | >120 |
|  | 3 | 32 | 30 × 30 | 9 | >120 |
|  | 4 | 37 | 30 × 30 | 29 | >120 |
|  | 5 | 21 | 30 × 30 | 17 | >116 |
|  | 6 | 36 | 30 × 30 | 15 | >120 |
| Total | 10 | 37 ± 11 | — | 14 ± 10 | >112 |

EXAMPLE 9

Analyses of Hemostasis and Platelet Function

Platelet aggregation studies were performed on blood obtained before and 30 minutes after antibody infusion. Such studies showed essentially complete abolition of aggregation in response to ADP (adenosine diphosphate, 9.1 uM), but the shape-change response remained intact. Platelet counts were obtained before and at the end of the experiment in 7 animals treated with monoclonal antibody fragments. There was a mean reduction in platelet count of 18% (range 3–33%). Bleeding times were obtained on 5 dogs before and 20 minutes after infusion with 7E3 antibody fragments. The values before the antibody infusion averaged 3.6±2.6 (range 1.5–5 minutes). After antibody infusion, one bleeding time was prolonged to 15 minutes, whereas the other four were greater than 30 minutes. In contrast, the bleeding time after treatment with a control monoclonal antibody in two dogs did not increase.

EXAMPLE 10

¹²⁵I-7E3 Antibody Binding Studies

¹²⁵I-7E3 antibody binding studies were performed on 6 dogs treated with the antibody before and 2 hours after antibody infusion. The binding decreased by 80±4% (SD) after infusion, indicating that this percentage of GPIIb/IIIa sites were blocked by the F(ab')₂ fragments in vivo. Despite this evidence of profound inhibition or platelet function and prolongation of the bleeding time, none of the dogs demonstrated clear evidence of excessive hemorrhage from their extensive operative wounds.

The rt-PA infusions did not produce significant systemic activation of the fibrinolytic system. The residual fibrinogen level measured towards the end of the infusion of 30 ug/kg/min of single chain rt-PA in blood samples collected on aprotonin was 92±19 percent (n=5) of the control value.

EXAMPLE 11

Pathological Examination

In order to perform a pathological examination, treated dogs were sacrificed with an overdose of pentobarbital. The left coronary artery was perfused with 2.5 percent glutaraldehyde solution in 0.1M cacodylate buffer (pH 7.4) under a pressure of 80–100 mm Hg for 15 min. The thrombosed and stenotic segments of the left anterior descending coronary artery were removed intact and fixation continued overnight. Appropriate cross sections at 2 mm intervals of both the damaged endothelial zone and of the stenosis were processed for light microscopy by staining with hemotoxilin/eosin, Van Giessen's elastic tissue staining and PTAH staining for muscle fibers and fibrin.

Pathological analysis with a light transmission microscope of cross-sections of the thrombosed segments of the left anterior descending coronary artery revealed intimal damage with interruption of the endothelial layer and occlusive thrombus. Following thrombolysis with rt-PA, endothelial damage was observed both at the side of the original thrombus and at the endothelial segment underlying the external constrictor.

Occasionally mural thrombus was observed overlaying the disrupted endothelium proximal to the stenosis and non-occlusive intraluminal thrombus was seen distal to the stenosis. Following reocclusion, occlusive thrombotic material, containing both platelets and fibrin, was observed in the area of maximal stenosis and just distal to it.

EXAMPLE 12

Comparison of Thrombolytic Potency and Effect on Reocclusion of Bolus Injections of rt-PA To compare the thrombolytic potency and effect on reocclusion of bolus injections of rt-PA alone with that of combined injections of rt-PA and monoclonal antibody 7E3 the animal model of Example 5 was employed.

Four repeated bolus injections of 450 ug/kg of rt-PA at 15 min intervals in 5 dogs (with high grade (over 90 percent) superimposed stenosis) caused transient reperfusion within 32±18 min (mean±SD) which was followed by cyclical long periods of reocclusion interspaced with short periods of reflow.

Injection of 0.8 mg/kg of monoclonal antibody 7E3 F(ab')$_2$ followed 10 min later by a single bolus injection of 450 ug/kg of rt-PA in dogs resulted in reperfusion within 5-10 min without reocclusion during an observation period of 2 hours.

Thus, combined bolus injections of the F(ab')$_2$ fragment of monoclonal antibody 7E3 and recombinant tissue-type plasminogen activator result in rapid coronary thrombolysis and abolish reocclusion.

Intravenous injection of a bolus containing the F(ab')$_2$ fragments of the monoclonal antibody 7E3 at a dose of 0.8 mg/kg in dogs may cause spontaneous thrombolysis during an observation period of two hours. Thus, myocardial infarctions may be treated solely through the administration of the F(ab')$_2$ fragment of antibody 7E3 without providing t-PA.

While the invention has been described in connection with specific embodiments thereof, it will be understood that it is capable of further modifications, and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of treatment for myocardial infarction which comprises providing to a patient in need of such treatment:
   a. a hapten-binding molecule capable of preventing potential reformation of fibrin-platelet clots, in an amount sufficient to prevent such reformation, said hapten-binding molecule being selected from the group consisting of
      (i) the monoclonal antibody 7E3, deposited as ATCC No. HB8832 and
      (ii) the F(ab')$_2$ fragment of the monoclonal antibody 7E3; in combination with
   b. a thrombolytic agent in an amount sufficient to either (i) dissolve a fibrin-platelet clot or (ii) inhibit the formation of a fibrin-platelet clot, wherein said hapten binding molecule (a) is different from said thrombolytic agent (b).

2. The method of claim 1 wherein both said hapten-binding molecule (a) and said thrombolytic agent (b) are provided to said patient by intravenous infusion.

3. The method of claim 1 wherein both said hapten-binding molecule (a) and said thrombolytic agent (b) are provided to said patient by bolus.

4. The method of claim 3 wherein said bolus is an intravenously injected bolus.

5. The method of claim 3 wherein said patient is provided with a first bolus containing said hapten-binding molecule (a) and a subsequently administered second bolus containing said thrombolytic agent (b).

6. The method of claim 4 wherein said patient is provided with a first bolus containing said hapten-binding molecule (a) and a subsequently administered second bolus containing said thrombolytic agent (b).

7. The method of any one of claims 1, 2, 3, or 6 wherein said thrombolytic agent is selected from the group consisting of streptokinase, prourokinase, urokinase and tissue-type plasminogen activator.

8. The method of claim 7 wherein said thrombolytic agent is tissue-type plasminogen activator.

9. The method of either of claims 1 or 2 wherein:
   (1) said hapten-binding molecule (a) is provided to said patient at a dose of between 0.01-0.8 mg per kg of patient weight, and
   (2) said thrombolytic agent (b) is provided to said patient at a dose of between 0.01-2.0 mg per kg of patient weight.

10. The method of any of claims 3, 4, 5, or 6 wherein:
    (1) said hapten-binding molecule (a) is provided to said patient at a dose of between 0.01-0.8 mg per kg of patient weight, and
    (2) said thrombolytic agent (b) is provided to said patient at a dose of between 0.01-1.0 mg per kg of patient weight.

11. A kit being compartmentalized in close confinement to receive two or more container means therein, which comprises:
    (1) a first container containing a therapeutically effective amount of a hapten-binding molecule capable of preventing potential reformation of fibrin-platelet clots, in an amount sufficient to prevent such reformation, said hapten-binding molecule being selected from the group consisting of
       (i) the monoclonal antibody 7E3, deposited as ATCC No. HB 8832 and
       (ii) the F(ab')$_2$ fragment of the monoclonal antibody 7E3; and
    (2) a second container containing a therapeutically effective amount of a thrombolytic agent in an amount sufficient to either (i) dissolve a fibrin-platelet clot or (ii) inhibit the formation of a fibrin-platelet clot, wherein said hapten-binding molecule (1) is different from said thrombolytic agent (2).

* * * * *